United States Patent [19]

Moore

[11] 4,386,205

[45] May 31, 1983

[54] RESOLUTION OF RACEMIC 5-PHENYL-2-PENTANOL

[75] Inventor: Bernard S. Moore, Waterford, Conn.

[73] Assignee: Pfizer Inc., New York, N.Y.

[21] Appl. No.: 313,560

[22] Filed: Oct. 22, 1981

[51] Int. Cl.$^3$ ............................................. C07D 491/22
[52] U.S. Cl. ....................................... 546/35; 560/98; 560/76; 568/810
[58] Field of Search .......................................... 546/35

[56] References Cited

U.S. PATENT DOCUMENTS 4,260,764  4/1981  Johnson .............................. 546/153

OTHER PUBLICATIONS

Prelog et al., Chemical Abstracts, vol. 51, 1114c, (1957).
Wilen, "Topics in Stereochemistry", edited by Allinger and Eliel, Wiley–Interscience, N.Y., vol. 6, pp. 141–143, (1971).

Primary Examiner—Paul M. Coughlan, Jr.
Attorney, Agent, or Firm—Charles J. Knuth; Albert E. Frost; Peter C. Richardson

[57] ABSTRACT

Resolution of racemic 5-phenyl-2-pentanol via the hemiphthalate ester, followed by diastereomer salt formation with (+)-brucine, separation of the brucine salt of (S)-5-phenyl-2-pentanol hemiphthalate and recovery of the (S)-alcohol therefrom. The (S)-5-phenyl-2-pentanol is a valuable intermediate for organic synthesis.

1 Claim, No Drawings

RESOLUTION OF RACEMIC 5-PHENYL-2-PENTANOL

BACKGROUND OF THE INVENTION

This invention relates to a process for resolution of racemic 5-phenyl-2-pentanol to (S)-5-phenyl-2-pentanol, a valuable intermediate in the synthesis of analgesic agents. More specifically, the process comprises esterifying racemic 5-phenyl-2-pentanol to form the hemiphthalate ester, followed by treating said ester with (+)-brucine, separating (S)-5-phenyl-2-pentylbrucine hemiphthalate salt, decomposing said salt to regenerate (S)-5-phenyl-2-pentylhemiphthalate, and hydrolyzing said ester to (S)-5-phenyl-2-pentanol.

The resolution of alcohols by converting them to hemiphthalate esters followed by diastereomer salt formation of said esters with an optically active base is described by Wilen in "Topics in Stereochemistry," edited by Allinger and Eliel, Wiley-Interscience, N.Y., Vol. 6, page 141 (1971).

The preparation of racemic 5-phenyl-2-pentanol by the reaction of 3-phenylpropylmagnesium bromide with acetaldehyde is reported by Roblin et al., J. Am. Chem. Soc. 57, 151–159 (1935).

It is a valuable intermediate for the synthesis of dl-5,6,6a-beta,7,8,9-alpha,10,10a-alpha-octahydro-1-acetoxy-9-hydroxy-6-beta-methyl-3-(1-alpha-methyl-4-phenylbutoxy)benzo[c]quinoline, an analgesic agent. The preparation of said compound and its use as an analgesic are described in U.S. Pat. No. 4,260,764, issued Apr. 7, 1981.

SUMMARY OF THE INVENTION

There has now been found a convenient and efficient method for resolving racemic 5-phenyl-2-pentanol to (S)-5-phenyl-2-pentanol. The process comprises preparing the hemiphthalate ester of racemic 5-phenyl-2-pentanol, separating the (S)-5-phenyl-2-pentylhemiphthalate therefrom as its (+)-brucine salt, followed by pH adjustment to remove the brucine component from said salt and then hydrolyzing the hemiphthalate ester to afford (S)-5-phenyl-2-pentanol which is recovered.

DETAILED DESCRIPTION OF THE INVENTION

The first step of the process, formation of the hemiphthalate ester of racemic 5-phenyl-2-pentanol, is readily accomplished by esterifying said 5-phenyl-2-pentanol with phthalic anhydride. The esterifiction is carried out by reacting the racemic 5-phenyl-2-pentanol with phthalic anhydide in equimolar proportions at a temperature of from about 90° C. to about 155° C. An excess of the 5-phenyl-2-pentanol can be used but is generally avoided for reasons of economy and to facilitate recovery of the ester.

The esterification can also be carried out in the presence of a reaction-inert solvent; that is, one which does not react to any appreciable extent with reactants or products, if desired. Representative solvents are aromatic hydrocarbons such as benzene and toluene.

The esterification can be conducted in the presence of an acid or base as catalyst. Catalytic amounts of dehydrating acids such as sulfuric, hydrochloric and p-toluenesulfonic acids are especially useful since they permit the reaction to proceed with satisfactory yields at temperatures of from 90°–98° C. and reduce reaction time, thus minimizing the amount of energy required.

The same is true as regards use of a base such as sodium acetate or pyridine. The term "catalytic amount" as used herein refers to from 0.1–0.5% of acid or base by weight of phthalic anhydride used. Pyridine can be used as solvent as well as catalyst and up to 2 moles of pyridine per mole of phthalic anhydride when used as solvent also minimizes the reaction period.

The use of greater than catalytic amounts of acid affords no advantage and is avoided since, as noted below, it must first be removed to minimize the amount of (+)-brucine used.

The use of catalytic amounts of acid or base does not interfere with the subsequent step comprising reaction of the ester with (+)-brucine. The use of larger amounts of acid would of course, require the use of more (+)-brucine than would otherwise by required. This is undesirable for economical reasons.

The use of greater than catalytic amounts of acid or base in the esterification step necessitates their removal by, for example, neutralization with an appropriate base or acid, followed by extraction of the ester according to known procedures.

For best results the esterification reaction is conducted in the absence of a solvent. The reaction mixture is heated to 90°–95° C. at about which temperature an exotherm occurs. When the exotherm occurs, the temperature is allowed to rise but is held below 155° C. by external cooling, if necessary. Following the exotherm the reaction is maintained and stirred at 130°–140° C. for about one hour. It is then cooled to about 50° C. and a reaction-inert solvent such as acetonitrile added to dissolve the reaction mixture. The resulting solution is used directly in the next step of the overall process.

The second step of the overall process comprises formation of the (+)-brucine salt of the racemic hemiphthalates by reaction with (+)-brucine. The reaction is carried out in a reaction-inert solvent such as acetonitrile at a temperature of from about 20° C. to the reflux temperature. It is generally advantageous to form the diasteromer salt at the upper side of this temperature range to accelerate salt formation. Higher temperatures can, of course, be used but appear to afford no advantage.

The brucine and hemiphthalate esters are desirably used in equimolar proportions although molar ratios of from about 1:1 to 0.8:1 are of value in achieving practical and economical recovery of the (S)-alcohol ester.

When salt formation is complete or essentially complete, as evidenced by formation of a clear or almost clear solution, a solvent such as isopropyl ether is added to precipitate the brucine salt of the (S)-alcohol hemiphthalate. In practice, especially for large scale preparations, the precipitating solvent is added to the brucine salt solution at the upper end of the temperature range and, following completion of the addition, the reaction cooled to precipitate the brucine salt of the (S)-alcohol ester, which is recovered by appropriate means, e.g., filtration.

The brucine salt of the (S)-alcohol hemiphthalate ester is then decomposed to regenerate brucine, which is recovered for further use, and the (S)-alcohol hemiphthalate. A convenient procedure comprises adjusting the pH of a mixture of said brucine salt, toluene, or other suitable water immiscible solvent, and water to a value of about 1.2 to 1.8. The aqueous phase containing brucine as an acid addition salt, e.g. brucine hydrochloride, is separated and brucine recovered therefrom by adjustment of the pH to about 11.5. The hemiphthalate ester of the (S)-alcohol is recovered from the toluene phase by standard procedures and recovered therefrom, if desired, by removal of toluene.

Solvents other than toluene can be used for the step of converting the brucine salt of the (S)-alcohol ester to the free ester and thence to the (S)- or chiral alcohol. The solvent should be immiscible with water and be a solvent for the hemiphthalate ester and for the alcohol itself. Representative of such other solvents are n-hexane, benzene, xylene, isopropyl ether, methylethyl ketone, n-butanol, ethyl acetate and chloroform.

In practice it is expedient to saponify the hemiphthalate ester directly in the toluene solution by treating said solution with aqueous alkali metal hydroxide, e.g. potassium or sodium hydroxide, to regenerate the (S)-alcohol which is recovered by removal of the solvent.

As those skilled in the art will recognize, the hemiphthalate ester can be converted to the alcohol by lithium aluminum hydride reduction. Additionally, the brucine salt can be treated directly with an alkoxide, such as sodium or potassium ethoxide, to generate the desired alcohol.

EXAMPLE 1

5-Phenyl-2-pentyl Hemiphthalate

Phthalic anhydride (21.53 kg., 145.28 mole) was stirred with racemic 5-phenyl-2-pentanol (23.86 kg., 145.27 mole) and heated to 90° C. The temperature was gradually increased to 130° C., an exotherm occurring at some point above 90° C. The temperature, when the exotherm occurs was not allowed to rise above 155° C. Following the exotherm, the reaction was maintained at 130°–140° C. for one hour, and then at the ambient temperature for 1.5 hours. It was then cooled to 50° C. and diluted with 125 liters of acetonitrile. The resulting solution of title product was used directly in the next step.

EXAMPLE 2

(S)-5-Phenyl-2-pentyl Brucine Hemiphthalate (+)-Brucine (57.55 kg., 145.27 moles) in 80.2 liters of acetonitrile was added to the acetonitrile solution of ester from the preceding Example and the mixture heated to 55°–60° C. Maintaining this temperature, isopropyl ester (620 liters) was added in a steady stream. The reaction was heated an additional 10 minutes following addition of the isopropyl ether. The solution was then cooled gradually to 23° C., and the crystalline material which began to form at 45°–55° C., granulated for 16 hours, recovered by filtration, washed with a mixture of acetonitrile (29 liters) and isopropyl ether (116.6 liters), then air dried at 55° C. (33 kg.). Highly resolved material has $[alpha]_D^{CHCl_3}$ +40.0. It was recrystallized from acetonitrile-isopropyl ether (for 33 kg. of crude, 132.5 liters of aceonitrile and 303 liters of isopropyl ether was used, with recovery of 26 kg. of purified title product).

EXAMPLE 3

(S)-5-Phenyl-2-pentanol

S-Brucine salt of the preceding Example (10.0 kg., 14.2 moles) was combined with 121 liters of toluene and 143.8 liters of water. With stirring the pH was adjusted to 1.7 by addition of about 6 liters of 3N HCl. The aqueous layer was separated and extracted with 2×37.85 liters of toluene. Brucine was precipitated from the aqueous layer by adjusting the pH to 11.5 with 50% NaOH. Recrystallization from isopropyl alcohol provides brucine suitable for reuse. The toluene layers were combined, back-washed with 75 liters of water, concentrated to 45 liters. Fresh water (65 liters) and then KOH (85%, 1.90 kg., 28.8 moles) were added and the mixture stirred for one hour at room temperature and then 2 hours at 82°–84° C. The reaction mixture was cooled to 25° C., the toluene layer separated and the aqueous layer washed 3×19 liters of toluene. The toluene layers were combined, washed 1×20 liters saturated NaCl, dried (MgSO$_4$), filtered and concentrated to yield title product as an oil (1.91 kg.), purified by distillation in vacuo (1.64 kg., b.p. 85°–92°/0.1 mm., $[alpha]_D^{25}$ +8.24 to +8.57°). Yield=20.4%.

EXAMPLE 4

Racemic 5-Phenyl-2-Pentyl Hemiphthalate

A mixture of racemic 5-phenyl-2-pentanol (404.5 g., 2.463 moles), phthalic anhydride (364.5 g., 2.463 moles) and dry pyridine (399.8 g., 5 moles) was stirred under a nitrogen atmosphere at ambient temperature for 5 minutes. It was then heated on a steam bath at 70° C. The internal temperature rose to 105° C., and after about 8 minutes, slowly dropped to 96° C. The reaction was stirred for 1.5 hours at 96° C., then cooled to 30° C. and poured into a flask containing toluene (3 liters) and water (3 liters) at 5° C. The pH was then adjustd to 1.2 by means of 12N HCl and the layers separated. The aqueous phase was extracted with toluene (1×1000 ml.) and the combined toluene extracts added to water (2 liters) at 10° C. The pH was lowered to 1.2 by means of 12N HCl, the toluene phase separated and washed with water (1×2 liters) and saturated aqueous sodium chloride solution (1×1 liter). It was then dried (MgSO$_4$) and concentrated in vacuo at 45°–50° C. internal temperature. Yield=757 g. (98%) of product as an oil.

EXAMPLE 5

Racemic 5-Phenyl-2-Pentyl Hemiphthalate

Under a nitrogen atmosphere a mixture of p-toluenesulfonic acid monohydrate (1.0 g., 5.3 mmoles), racemic 5-phenyl-2-pentanol (292 g., 1.78 moles) and phthalic anhydride (263 g., 1.78 moles) was heated at an internal temperature of 95°–98° C. for 2 hours. It was then cooled to room temperatue to give a quantitative yield of the title product as a clear, viscous oil.

Ester prepared by this procedure was used directly in the procedure of Example 6.

EXAMPLE 6

(+)-Brucine Salt of (S)-5-Phenyl-2-Pentyl Hemiphthalate

A mixture of racemic 5-phenyl-2-pentyl hemiphthalate (720 g., 2.305 moles), (+)-brucine (901 g., 2.29 moles) and acetonitrile (4 liters) was stirred at ambient temperature for 5 minutes and then at 80°–82° C. for 5 minutes to give a clear solution. Isopropyl ether (11.6 liters) was then added to the solution over a 15 minute period while maintaining the internal temperature at 64° C. The resulting cloudy solution was then seeded with 5 g. of brucine salt (Example 2) and allowed to cool slowly (35 minutes) to 45° C. at which point rapid crystallization occurred. The reaction was allowed to cool to 23° C. and stirred overnight. The tan crystalline salt was recovered by filtration, washed with isopropyl ether-acetonitrile (2 liters of 3:1), then with isopropyl ether (2 liters) and air dried. Yield=601 g. (74%). M.P.=114°-121° C. (wet melt).

The salt (600 g.) thus produced was recrystallized by dissolving it in acetonitrile (1.8 liters) at 70° C. and then slowly adding isopropyl ether (5.4 liters) over a 30 minute period while maintaining the internal temperature at 60°-64° C. Crystallization occurred almost immediately. The slurry was gradually cooled to 23° C. and the crystals granulated for one hour. Filtration of the crystals followed by successive washes with isopropyl ether-acetonitrile (1 liter of 3:1) and isopropyl ether (1 liter) and air drying of the filter cake gave 525 g. (88%) yield. M.P.=111°-122° C.

EXAMPLE 7

Hemiphthalate Ester of (S)-5-Phenyl-2-Pentanol

A mixture of the brucine salt of Example 6 (523 g., 0.74 mole), toluene (4 liters) and water (7.4 liters) was cooled to an internal temperature of 8° C. and adjusted to pH 1.3 by slow addition of 3N HCl. It was stirred for 5 minutes and the phases separated. The aqueous phase was extracted with toluene (2×2 liters), the combined toluene phases stirred with water (3.6 liters) and the pH lower to 1.3 by addition of 3N HCl. The toluene phase was separated and washed successively with water (1×3.6 liters) and saturated aqueous sodium chloride solution (1×3.6 liters). The toluene phase was then dried (MgSO$_4$) and concentrated in vacuo to give 235 g. (101.7%) of the title product. (The product was estimated by nuclear magnetic resonance spectroscopy to contain about 10-12% toluene by weight).

EXAMPLE 8

(S)-5-Phenyl-2-Pentanol

A mixture of the hemiphthalate ester of (S)-5-phenyl-2-pentanol (222 g. of the product of Example 7), toluene (2.2 liters), water (3.2 liters) and sodium hydroxide pellets (53 g., 1.33 moles) was stirred at ambient temperature for 35 minutes and then heated at 82°-84° C. for 2 hours. The reaction was cooled to 25° C. and the layers separated. The aqueous phase was extracted with toluene (1×1000 ml and 2×400 ml.). The toluene extracts were combined, washed with water (1×1000 ml.), then with saturated aqueous sodium chloride solution and dried (MgSO$_4$). Removal of the toluene in vacuo gave 97.2 g. of the chiral alcohol. Vacuum distillation afforded the pure product [alpha]$_D^{25}$ +8.45 (C=1, CHCl$_3$).

PREPARATION A d,1-5-Hydroxy-2-beta-methyl-7-(1-alpha-methyl-4-phenylbutoxy)-4-oxo-1,2,3,4-tetrahydroquinoline A mixture of (S)-5-phenyl-2-pentanol (164 g., 1 mole), triethylamine (280 ml., 2 moles) and dry tetrahydrofuran (800 ml.) under a nitrogen atmosphere was cooled in an ice/water bath. Methanesulfonyl chloride (85 ml., 1.1 moles) in dry tetrahydrofuran (200 ml.) was added dropwise at such a rate that the temperature remained essentially constant. The mixture was allowed to warm to room temperature and was then filtered to remove triethylamine hydrochloride. The filter cake was washed with dry tetrahydrofuran and the combined wash and filtrate evaporated under reduced pressure to give the product as an oil. The oil was dissolved in chloroform (1 liter) and the solution washed with water (2×1 liter) and then with saturated brine (1×200 ml.). Evaporation of the solvent afforded the mesylate of (S)-5-phenyl-2-pentanol which was used in the next step without further purification.

A mixture of d,1-5,7-dihydroxy-2-beta-methyl-4-oxo-1,2,3,4-tetrahydroquinoline (114.8 g., 0.594 mole), potassium carbonate (174.8 g., 1.265 moles), N,N-dimethylformamide (612 ml.) and (S)-5-phenyl-2-pentanol mesylate (165.5 g., 0.638 mole), under a nitrogen atmosphere, was heated to 80°-82° C. in an oil bath for 1.75 hours. The mixture was cooled to room temperature and then poured into ice/water (4 liters). The aqueous solution was extracted with ethyl acetate (2×4 liters) and the combined extracts washed successively with water (4×2 liters) and saturated brine (1×2 liters), then dried (MgSO$_4$), decolorized with charcoal and evaporated to give the product.

PREPARATION B d,1-1-Formyl-5-hydroxy-3-hydroxymethylene-2-beta-methyl-7-(1-alpha-methyl-4-phenylbutoxy)-4-oxo-1,2,3,4-tetrahydroquinoline A solution of d,1-5-hydroxy-2-beta-methyl-7-(1-alpha-methyl-4-phenylbutoxy)-4-oxo-1,2,3,4-tetrahydroquinoline (195 g., ca. 0.58 mole) in ethyl formate (1140 g., 14.6 moles) was added dropwise to sodium hydride (72 g., 3.0 moles, obtained by washing 144 g. of 50% sodium hydride with hexane, 3×500 ml.), with good stirring. After about 1.5 hours when 2/3 of the ethyl formate solution had been added, the addition was discontinued to allow the vigorous foaming to subside. Diethyl ether (600 ml.) was added and the mixture stirred for 15 minutes before adding the remainder of the ethyl formate solution. When addition was complete, diethyl ether (600 ml.) was added, the reaction mixture stirred for an additional 10 minutes and then poured onto ice water (2 liters). It was acidified to pH 1 with 10% HCl and the aqueous phase separated and extracted with ethyl acetate (2×2 liters). The combined organic solutions were washed successively with water (2×2 liters), brine (1×1 liter) and dried (MgSO$_4$). Concentration gave the product as a red-brown oil which was used without further purification.

PREPARATION C d,1-1-Formyl-5-hydroxy-2-beta-methyl-7-(1-alpha-methyl-4-phenylbutoxy)-4-oxo-3-(3-oxobutyl)-1,2,3,4-tetrahydroquinoline To a solution of d,1-1-formyl-3-hydroxymethylene-5-hydroxy-2-beta-methyl-(1-alpha-methyl-4-phenylbutoxy)-4-oxo-1,2,3,4-tetrahydroquinoline (229 g., ca. 0.58 mole) in methanol (880 ml.) under a nitrogen atmosphere was added triethylamine (27.2 ml.) with stirring. Methyl vinyl ketone (97.0 ml.) was then added and the mixture stirred overnight at room temperature.

The reaction was complete at this point and comprised a mixture of the title compound and the corresponding 1,3-diformyl derivative. To convert the diformyl compound to the desired title compound, the reaction mixture was diluted with ether (6 liters) and then washed successively with 10% aqueous sodium carbonate (4×1700 ml.), brine (1×2 liters) and then dried (MgSO$_4$). Concentration of the solution afforded a red-brown oil. The oil was dissolved in methanol (1920 ml.) and the solution cooled to 0° C. Potassium carbonate (21.2 g.) was added, the mixture stirred for 3 hours at 0° C. and then treated with acetic acid (18.7 g.). The methanol was removed under reduced pressure and the resultant oil stirred with water (2 liters) and ethyl acetate (2 liters) for 10 minutes. The aqueous phase was separated, extracted with ethyl acetate (1×2 liters) and the combined ethyl acetate solutions washed with water (2×2 liters), brine (1×2 liters) and dried (MgSO$_4$). Concentration under reduced pressure and chromatography of the concentrate on silica gel (1.8 kg.) gives the title product.

PREPARATION D d,1-5,6,6a,7-Tetrahydro-1-hydroxy-6-beta-methyl-3-(1-alpha-methyl-4-phenylbutoxy)-benzo[c]quinolin-9(8H)-one A solution of d,1-1-formyl-5-hydroxy-2-beta-methyl-7-(1-alpha-methyl-4-phenylbutoxy)-4-oxo-3-(3-oxobutyl)-1,2,3,4-tetrahydroquinoline (174 g., 0.398 mole) in methanolic 2N KOH (5.9 liters) and methanol (5.9 liters) was stirred and heated at reflux overnight under a nitrogen atmosphere. To the cooled solution was added acetic acid (708 g.) dropwise with stirring over a 15 minute period. The resulting solution was concentrated by rotary evaporation (in vacuo, water aspirator) to a semi-solid which was filtered and washed first with water to remove potassium acetate and then with ethyl acetate until all the black tar was removed. Recrystallization from hot ethyl acetate afforded the pure product.

PREPARATION E d,1-trans-5,6,6a-beta,7,8,9,10,10a-alpha-octahydro-1-acetoxy-9-beta-hydroxy-6-beta-methyl-3-(1-alpha-methyl-4-phenylbutoxy)benzo[c]quinoline A hetereogeneous mixture of d,1-5,6,6a,7-tetrahydro-1-acetoxy-6-beta-methyl-3-(1-alpha-methyl-4-phenylbutoxy)benzo[c]quinolin-9(8H)-one (3.0 g., 7 mmole) and palladium-on-carbon (5%, 3.0 g.) in methanol (30 ml.) was hydrogenated at room temperature in a Parr apparatus under 50 p.s.i. hydrogen for three hours. The catalyst was then filtered and the methanol filtrate evaporated under reduced pressure to give the title product.

The product was taken up in ethyl acetate (300 ml.) and the resulting solution cooled to 0° C. An excess of a saturated solution of hydrogen chloride in ethyl acetate was then added to precipitate the hydrochloride salt of the title product as a white solid. It was filtered, washed with ethyl acetate, and dried.

The d,1-5,6,6a,7-tetrahydro-1-acetoxy-6-beta-methyl-3-(1-alpha-methyl-4-phenylbutoxy)benzo[c]-quinolin-9(8H)-one was prepared as follows:

To a stirred solution of d,1-5,6,6a,7-tetrahydro-1-hydroxy-6-beta-methyl-3-(1-alpha-methyl-4-phenylbutoxy)benzo[c]quinolon-9(8H)-one (4.5 g., 0.0115 mole) in pyridine (45 ml.) at room temperature was added acetic anhydride (45ml.). The resulting solution was stirred for 3.5 hours and then poured onto ice-water (250 ml.) and the mixture extracted with diisopropyl ether (2×250 ml.). The combined extracts were washed with water (3×200 ml.), dried (MgSO$_4$) and evaporated under reduced pressure to a yellow-brown oil which solidified on scratching the walls of the flask containing it. Trituration of the solid with n-heptane followed by recrystallization from hot chloroform-n-hexane (1:4) gave the pure ester.

I claim:

1. The (+)-brucine salt of (S)-5-phenyl-2-pentyl hemiphthalate.

* * * * *